(12) United States Patent
Schuler et al.

(10) Patent No.: US 6,775,573 B2
(45) Date of Patent: *Aug. 10, 2004

(54) ELECTRICAL METHOD TO CONTROL AUTONOMIC NERVE STIMULATION OF GASTROINTESTINAL TRACT

(75) Inventors: Eleanor L. Schuler, Rio Rancho, NM (US); Claude K. Lee, Reno, NV (US)

(73) Assignee: Science Medicus Inc., Reno, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/085,386

(22) Filed: Feb. 28, 2002

(65) Prior Publication Data

US 2003/0212439 A1 Nov. 13, 2003

Related U.S. Application Data

(60) Provisional application No. 60/271,948, filed on Mar. 1, 2001.

(51) Int. Cl.[7] .................................................. A61N 1/00
(52) U.S. Cl. ........................................................ 607/40
(58) Field of Search .................................... 607/40, 41

(56) References Cited

U.S. PATENT DOCUMENTS 6,238,423 B1 * 5/2001 Bardy ......................... 607/40
6,633,779 B1 * 10/2003 Schuler et al.

* cited by examiner

Primary Examiner—Scott Getzow
(74) Attorney, Agent, or Firm—Barnes & Thornburg

(57) ABSTRACT

A method and device for controlling autonomic or sympathic nerve stimulation of the gastrointestinal tract. The method comprises selecting waveforms from a storage area that are representative of body organ function. The selected waveforms are then transmitted to a treatment member, which is in direct contact with the body or attached to internal targets, and which then broadcasts the waveforms to a specific body organ to modulate the body organ functioning. A control module is provided for transmission to the treatment member. The control module contains waveforms which are selected and transmitted to the treatment member, and computer storage can be provided for greater storage capacity and manipulation of the waveforms.

10 Claims, 2 Drawing Sheets

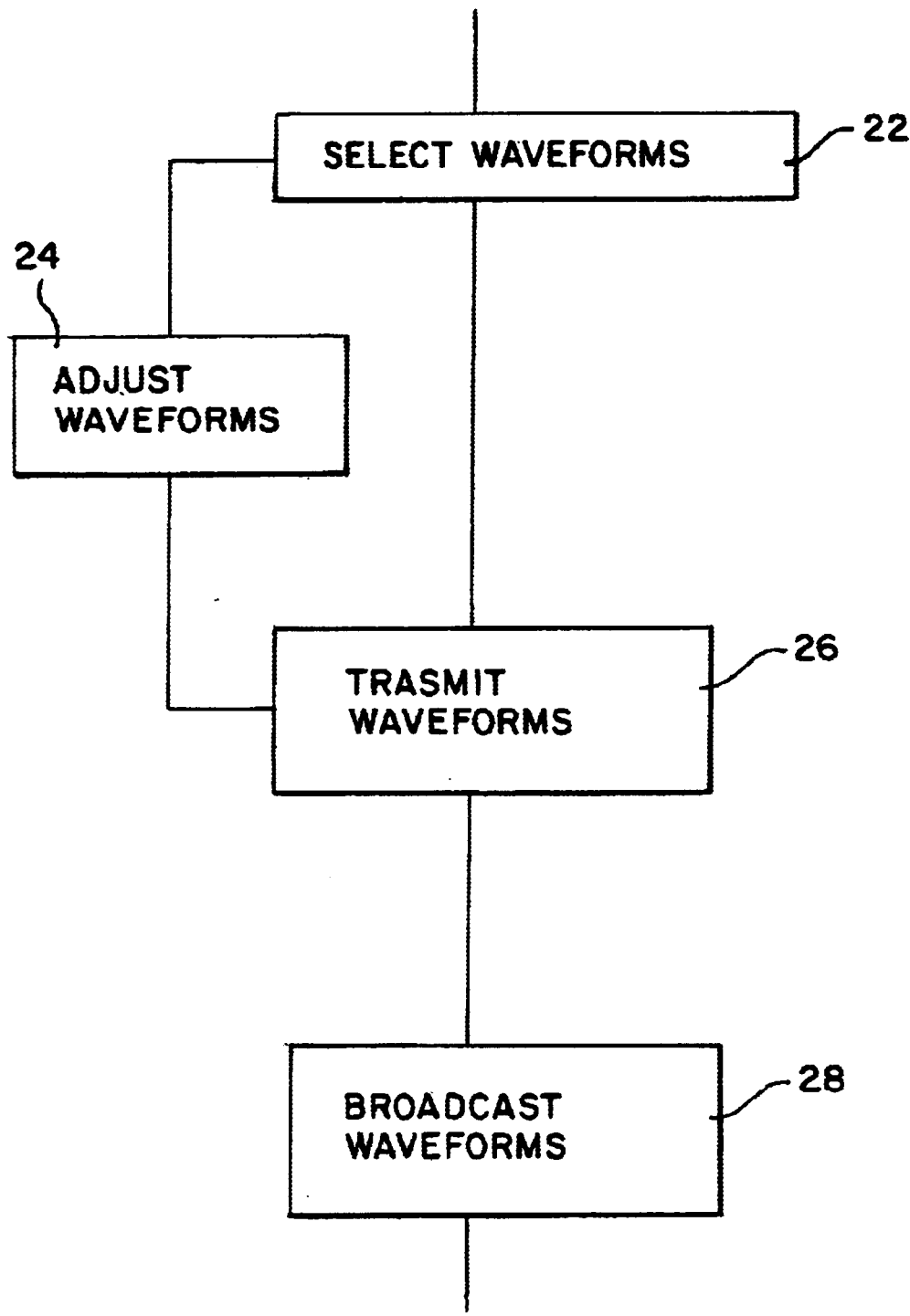

ELECTRICAL METHOD TO CONTROL AUTONOMIC NERVE STIMULATION OF GASTROINTESTINAL TRACT

RELATED APPLICATION

This is the non-provisional filing of application Ser. No. 60/271,948, filed on Mar. 1, 2001, entitled "Electrical Method to Control Autonomic Nerve Stimulation of Gastrointestinal Tract."

BACKGROUND OF THE INVENTION

This invention concerns the ability to electrically regulate the function and actions of the gastrointestinal system. Specifically, this invention is concerned with the muscle action of the small and large intestines and the production of enzymes and hormones by means of specifically coded electrical waveforms, which emulate the natural coded signals that normally control the gastrointestinal tract. The invention is aimed at modulating the autonomic nerve signals along or at critical nervous pathways by conducting or broadcasting low-voltage shaped signals so as to regulate, modulate or alter peristalsis activities and other digestive events for the benefit of the owner of the intestines.

The human and animal autonomic nervous system functions principally by operating the vegetative systems concerned with respiration, blood circulation and digestion. The brain provides central processing of information coming to it from the afferent nerve sensors and then makes a selection from stored signals in the brainstem that will turn on or off or modulate target organs. Once the specific signal selection is made then efferent instructional signals are sent on their way to do their regulatory work. In this application the focus is on modulating autonomic action in the digestive system.

The digestive regulatory action of this invention spans ability for modulation, demodulation, phase angle modulation, amplitude variation and blanking of either or both afferent and efferent electrical waveform codes concerning vegetative life activities of the digestive system. Gastrointestinal processing, including chemical participation at the neural synapses, muscular activity, enzyme and hormonal availability and the timing of all such events can be regulated with appropriate electrical signals. The invention utilizes emulated electrical codes for the purpose of improving the digestive process and to treat disorders with low voltage signals, which are conducted or broadcast into appropriate nervous segments.

The gastrointestinal ("GI") function is to process consume food, to extract nutrients and to dispose of waste products of digestion. The digestive system is a twisted and shaped tube that starts with the mouth, throat, gullet (esophagus), stomach, ileum (small intestine), colon (large intestine), rectum and anus. This muscular tube is some 25 feet long with most of it coiled within the abdomen.

The inner layer of the tubal digestive system has a mucus layer that secretes enzymes, and other chemicals to aid digestion. There is a sub mucosal layer located directly beneath the mucus producing layer that is rich in blood vessels, networks of nerves and lymph vessels. This is where we find the reticuloendothelial tissue whose job it is to provide immune services against microbial infection and further services in ridding the body of cellular debris. Beneath the mucosal and sub-mucosal layers are the muscular layers consisting of two parts. It has circular and longitudinal muscles with some oblique control so that it can pass food down the tube while also mashing it. All of these layers operate in response to the autonomic nervous system. Absorption of nutrients occurs by diffusion, carrier transport or endocytosis.

Digestion begins in the mouth where the teeth reduce large food chunks to smaller pieces and saliva helps turn the food into a semi-liquid mass. This is swallowed into the 10 inches of esophagus at the rate of 2 or 3 inches per second to arrive at the stomach. The activity of the stomach is a back and forth mixing action where as the intestinal tract uses a motion that moves the food in one direction, downward. The stomach tends to contract at its entrance so as to prevent food from moving back into the esophagus and tends to propel the digesting food toward the pylorus of the stomach.

The action of the stomach is to mix enzymes, hormones and other secretions to produce what is now called chyme. The contraction at the pylorus (distal end of the stomach) allows finished acidified chyme to gradually leak into the duodenum (first 10 inches of the small intestine) while retaining solid food and continuing the back and forth mixing (much like a washing machine) in the stomach proper until it is small enough (particles of about 0.3 mm in size) to be accepted for intestinal processing.

The control of acid and enzyme secretion in the stomach is a delicate balance that depends on the appearance and nature of the food available. The autonomic nervous system controls this activity in the stomach via afferent sensors and efferent nerves. The most important nerve is the vagus nerve bundle, containing both afferent and efferent pathways, which travels all the way from the medulla oblongata of the brain, to direct digestive operations, especially codes for the secretion of digestive chemicals. The medulla also influences the salivary glands of the oral cavity that begins, with chewing, the food digestive process.

The passage of food down the gastrointestinal tract of humans and animals depends on a peristaltic reflex in each of the digestive organs. Peristalsis in the gastrointestinal tract involves muscular control of the tubal structures so as to mix and propel digestive product along a pathway at speeds that vary to allow the process to properly function. The peristaltic movements are paced in a worm-like and constrictive manner as directed by the nervous system coded instructions.

The small intestine is where the acidic chyme is gradually neutralized and becomes slightly alkaline as it is bombarded by a battery of enzymes from the pancreas including chymotrypsin and trypsin. Bile enters from the gallbladder to emulsify fats. Finger-like projections inside the small intestine have been formed by wrinkling the mucus membrane into epithelial folds. Each such fold contains projections called villi with micro-villi to absorb products of digestion.

The pancreas, acting as an exocrine gland, produces enzymes that aid in the digestion of fats, carbohydrates, proteins and nucleic acids. In addition the pancreas secretes a fluid high in bicarbonate, thusly neutralizing some of the stomach acid to avoid erosion of the intestinal linings. Acting as an endocrine gland, the pancreas secretes three hormones, glucagon, somatostatin and insulin, to manage the level of glucose, all being ordered by code electrical signs from the medulla oblongata.

After about 8 to 10 hours the digestive process is completed and has allowed for absorption of the available nutrients in the small intestine. The digestive product enters a structure at the end of the small intestine called the ileum, where it empties into the colon. Since all of the nutrients were absorbed in the small intestine all that remains are the waste products and a lot of water for the colon to deal with. As the colon absorbs the water its peristaltic action forms a stool while moving the waste product toward the rectal pouch and anus.

The act of defecating is a combination of reflex reactions and conscious control of three sheet muscles. The first is involuntary and the later two are under some voluntary control. The waste product is composed of digestible or indigestible food plus mucus, bacteria and water. Its brownish color is due to bile pigment and its odor comes from the bacterial breakdown products. Also present are colonic gases that are a combination of swallowed air, byproducts of the digestive process and considerable gases produced by chemical activities of resident bacteria.

Electrical signaling has played a pivotal part in operating the digestive process and has provided signals for the production of secretions needed for digestion. Most of these signals are autonomic and conduct their job with little conscious participation.

SUMMARY OF THE INVENTION

The invention provides a method for controlling autonomic nerve stimulation of the gastrointestinal tract. Stored waveforms that are generated and carried in the body are selected from a storage area. The selected waveforms are then transmitted to a treatment member which is in direct contact with the body. The treatment member then broadcasts the selected waveforms to an organ in the body.

The waveforms may be selected from a storage area in a computer, such as a scientific computer. The process of transmitting the selected waveforms can either be done remotely or with the treatment member connected to a control module. The transmission may be seismic, electric, or via any other suitable method.

The invention further provides an apparatus for controlling autonomic nerve stimulation of the gastrointestinal tract. The apparatus includes a source of collected waveforms that are indicative of body organ functioning, a treatment member in direct contact with the body, means for transmitting collected waveforms to the treatment member to a body organ.

The transmitting means may include a digital to analog converter. The source of collected waveforms preferably comprises a computer which has the collected waveforms stored in digital format. The computer may include separate storage areas for collected waveforms of different categories.

The treatment member may be comprised of an antenna or an electrode, or any other means of broadcasting one or more waveforms directly to the body.

BRIEF DESCRIPTION OF THE DRAWINGS

The invention is described in greater detail in the following description of examples embodying the best mode of the invention, taken in conjunction with the drawing figures, in which:

FIG. 3 is a flow chart of the method according to the invention.

DESCRIPTION OF EXAMPLES EMBODYING THE BEST MODE OF THE INVENTION

Figure 1:
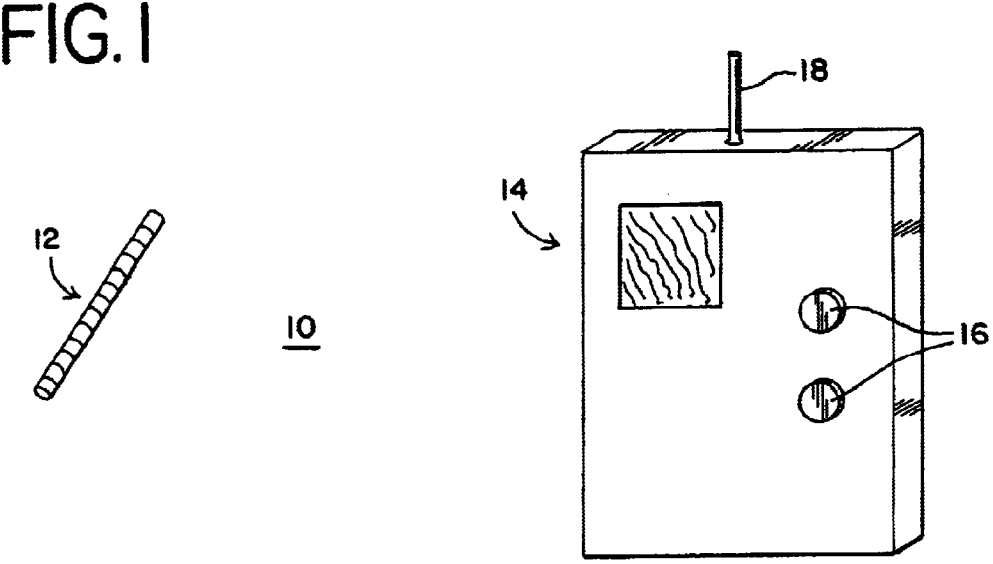
FIG. 1 is a schematic diagram of one form of apparatus for practicing the method according to the invention.

For the purpose of promoting an understanding of the principles of the invention, references will be made to the embodiments illustrated in the drawings. It will, nevertheless, be understood that no limitation of the scope of the invention is thereby intended, such alterations and further modifications in the illustrated device, and such further applications of the principles of the invention illustrated herein being contemplated as would normally occur to the one skilled in the art to which the invention relates.

This invention makes use of and focuses on the fact that the human body is both electrical and chemical in its internal operation. However, the electrical function, which has been principally explored in the anatomy and physiology laboratory, is only now able to emerge as a new technology because of the advances in neuroscience, electrical engineering and computer science. The pharmaceutical industry has been supplying beneficial chemical treatment for over a century. The inventors anticipate that electrical treatment possibilities will move toward the forefront with the availability of accurately emulated waveforms as described in this invention and the below mentioned sister applications.

All coded signals operate at less than 1 volt, naturally. Applied voltage may be up to 20 volts according to the invention to allow for voltage loss during the transmission or conduction of the required coded signals. Current should always be less than 2 amp output. Direct conduction into the nerves via electrodes connected directly to such nerves will likely have outputs of less than 3 volts and current of less than one tenth of an amp.

The invention encompasses both a device and a method for controlling autonomic nerve stimulation of the gastrointestinal tract by means of neuro-receptive waveforms. One form of a device 10 for controlling autonomic nerve stimulation of the gastrointestinal tract, as shown in FIG. 1, is comprised of at least one treatment member 12, and a control module 14. The treatment member 12 is in direct contact with a body and receives a coded electrical waveform from the control module 14. The treatment member 12 may be an electrode, antenna, a seismic transducer, or any other suitable form of conduction attachment for broadcasting autonomic nerve signals that regulate or operate gastrointestinal functions in humans or animals. The treatment member 12 may be attached to appropriate nerves in a surgical process. Such surgery may be accomplished with "key-hole" entrance in a gastrointestinal procedure. If necessary a more expansive gastrointestinal operation may be required for more proper placement of the treatment member 12. Waveform signals known to control gastrointestinal functioning may then be sent into nerves that are in close proximity with the brain stem. Nerve targets can be of the sympathic or autonomic system.

The control module 14 is comprised of at least one control 16, and an antenna 18. The control 16 allows the device to regulate the signal transmission into the body. As shown in FIG. 1, the control module 14 and treatment member 12 can be entirely separate elements allowing the device 10 to be operated remotely, or, in appropriate circumstances, there may be direct connection. The control module 14 can be unique, or can be any conventional device that can provide appropriate waveform signals for transmission to the treatment member 12.

Figure 2:
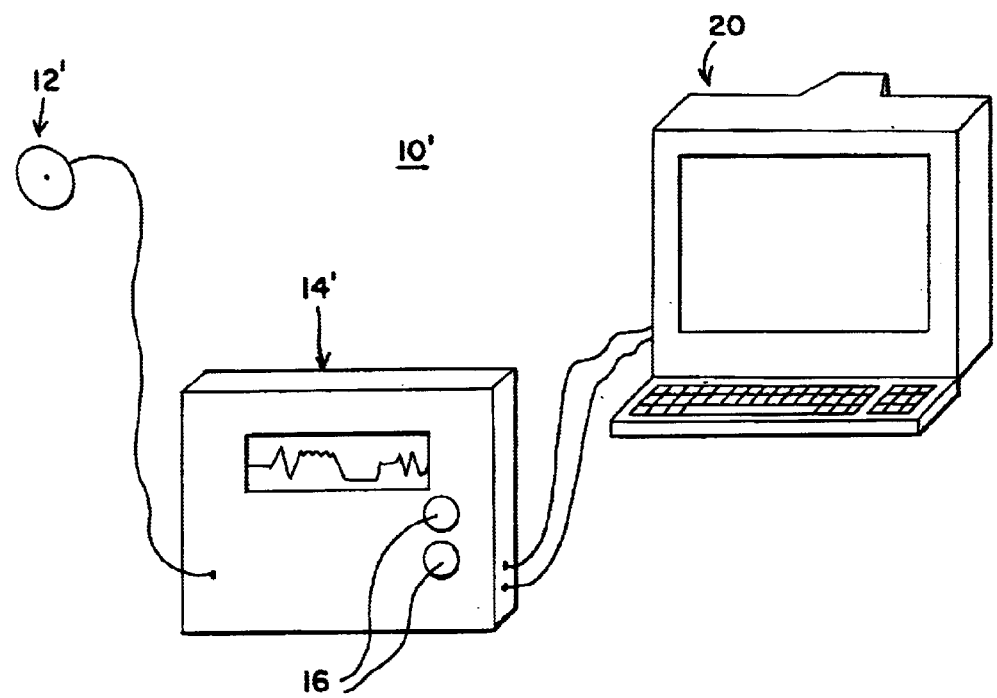
FIG. 2 is a schematic diagram of another form of apparatus for practicing the method according to the invention.

In an alternate embodiment 10' of the device 10, as shown in FIG. 2, the control module 14' and treatment member 12' are connected. Similar members retain the same reference numerals in this figure. Additionally, FIG. 2 further shows another embodiment of the device 10' as being connected to a computer 20, which provides greater capacity to store the waveform signals. The output voltage and amperage provided by the device 10' during treatment should not exceed 20 volts nor 2 amps for each signal.

The computer 20 is used to store the unique waveform signals, which are complex and unique to each organ and function of such organ or organ system. It is a waveform signal(s) selected from the stored library of waveforms in the computer 20 that is transmitted to the control module 14' and used for treatment of a patient.

The waveform signals, and their creation, are described in greater detail in U.S. patent application Ser. No. 10/000005, filed on Dec. 4, 2001, and entitled "Device and Method to Record, Store, and Broadcast Specific Brain Waveforms to Modulate Body Organ Functioning," the disclosure of which is incorporated herein by reference. Such application contains representative types of waveforms that are also operative in the control of human or animal gastrointestinal processes. Such waveforms or any combination of segments of the waveforms presented in the above mentioned patent application are representative of the kinds of signals operating with the neuron circuits emanating from the medullopontine region of the brain. Such waveforms can be used to modulate either afferent or efferent nerves that play a part in the control or fine-tuning of gastrointestinal processes. Such waveform signals are similar to those naturally produced by the brain stem structures for modulating gastrointestinal processes, as described in detail in the immediately above-identified incorporated application.

The invention further includes a method, as shown in FIG. 3, for using the device 10, 10' to control autonomic nerve stimulation of the gastrointestinal tract. The method begins at step 22 by selecting one or more stored coded electrical waveform signals from a menu of cataloged waveform signals. The waveform signals selected control and stimulate gastrointestinal functions. Such waveform signals are similar to those naturally produced by the brain stem structures for controlling and stimulating gastrointestinal processes. Once selected, the waveform signals may be adjusted, in step 24, to perform a particular function in the body. Alternatively, if it is decided that the waveform signals do not need to be adjusted, step 24 is skipped and the process proceeds directly with step 26. At step 26, the waveform signal is transmitted to the treatment member 12, 12' of the device 10, 10'.

Upon receipt of the waveform signals, the treatment member 12, 12' broadcasts the waveform signals to the appropriate location, as shown in step 28. The device 10, 10' utilizes appropriate waveform signals to stimulate or control gastrointestinal action via conduction or broadcast of electrical signals into selected nerves or components of gastrointestinal system. It is believed that target organs can only uniquely "hear" their own individual waveform. As a result, the body is not in danger of having one organ perform the function of another organ simply because the first organ received the second organ's waveform.

In one embodiment of the invention, the process of broadcasting by the treatment member 12, 12' is accomplished by direct conduction or transmission through unbroken skin in a selected appropriate zone on the neck, head, or torso. Such zone will approximate a position close to the nerve or nerve plexus onto which the signal is to be imposed. The treatment member 12, 12' is brought into contact with the skin in a selected target area that allows the transport of the signal to the target nerve. Otherwise, connections are made internally at appropriate points.

In an alternate embodiment of the invention, the process of broadcasting the waveform is accomplished by direct conduction via attachment of an electrode to the receiving nerve or nerve plexus. This requires a conventional surgical intervention as required to physically attach the electrode to the selected target nerve.

In yet another embodiment of the invention, the process of broadcasting is accomplished by transposing the waveform into a seismic form where it is sent into a region of the head, neck, or torso in a manner that allows the appropriate "nerve" to receive and to obey the coded instructions of such seismic signal. The treatment member 12, 12' is pressed against the unbroken skin surface using an electrode conductive gel or paste medium to aid conductivity.

Various features of the invention have been particularly shown and described in connection with the illustrated embodiments of the invention. However, it must be understood that these particular products, and their method of manufacture, do not limit but merely illustrate, and that the invention is to be given its fullest interpretation within the terms of the appended claims.

We claim:

1. A method for controlling autonomic nerve stimulation of the gastrointestinal tract comprising the steps of:
   a. selecting from a storage area one or more waveforms generated in the body and carried by neurons in the body;
   b. transmitting or conducting the selected waveforms to a treatment member in contact with the body; and
   c. broadcasting the selected waveforms from the treatment member to an organ in the body.

2. The method according to claim 1, in which step "a" further includes selecting said waveforms from a storage area in a computer.

3. The method according to claim 1, in which step "b" further comprises transmitting the selected waveforms remotely to the treatment member.

4. The method according to claim 1, in which step "b" further comprises transmission of the selected waveforms.

5. An apparatus for controlling autonomic nerve stimulation of the gastrointestinal tract, comprising:
   a. a source of collected waveforms indicative of body organ functioning;
   b. a treatment member in direct contact with the body;
   c. means for transmitting one or more of the collected waveforms to the treatment member; and
   d. means for broadcasting the collected waveforms from the treatment member to a body organ to stimulate organ function.

6. The apparatus according to claim 5, in which said transmitting means includes a digital to analog converter.

7. The apparatus according to claim 5, in which said source comprises a computer having collected waveforms stored in digital format.

8. The apparatus according to claim 7, in which said computer includes separate storage areas for collecting waveforms of different respiratory functional categories.

9. The apparatus according to claim 5, in which the treatment member comprises an antenna for broadcasting respiratory signals.

10. The apparatus according to claim 5, in which the treatment member comprises an electrode.

* * * * *

UNITED STATES PATENT AND TRADEMARK OFFICE
CERTIFICATE OF CORRECTION

PATENT NO. : 6,775,573 B2  
APPLICATION NO. : 10/085386  
DATED : August 10, 2004  
INVENTOR(S) : Eleanor L. Schuler and Claude K. Lee It is certified that error appears in the above-identified patent and that said Letters Patent is hereby corrected as shown below:

Column 6, lines 58 and 61, "respiratory" should be changed to --gastrointestinal--.

Signed and Sealed this

Fifth Day of September, 2006

JON W. DUDAS  
*Director of the United States Patent and Trademark Office*